United States Patent
Berning et al.

(10) Patent No.: US 7,226,636 B2
(45) Date of Patent: Jun. 5, 2007

(54) GOLD-COATED NANOPARTICLES FOR USE IN BIOTECHNOLOGY APPLICATIONS

(75) Inventors: Douglas E. Berning, Los Alamos, NM (US); Robert H. Kraus, Jr., Los Alamos, NM (US); Robert W. Atcher, Los Alamos, NM (US); Jurgen G. Schmidt, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 130 days.

(21) Appl. No.: 10/631,104

(22) Filed: Jul. 31, 2003

(65) Prior Publication Data
US 2005/0025969 A1  Feb. 3, 2005

(51) Int. Cl.
*B05D 7/14* (2006.01)

(52) U.S. Cl. .................. 427/132; 427/216; 427/217

(58) Field of Classification Search ........... 427/217, 427/132, 212, 216; 75/369, 428
See application file for complete search history.

(56) References Cited

U.S. PATENT DOCUMENTS

| | | | | |
|---|---|---|---|---|
| 5,512,317 | A * | 4/1996 | Blagev | 427/215 |
| 6,045,925 | A * | 4/2000 | Klabunde et al. | 428/548 |
| 6,103,868 | A * | 8/2000 | Heath et al. | 528/482 |
| 6,530,944 | B2 * | 3/2003 | West et al. | 607/88 |
| 6,589,629 | B1 * | 7/2003 | Bao et al. | 428/144 |
| 6,592,938 | B1 * | 7/2003 | Pessey et al. | 427/212 |
| 6,685,986 | B2 * | 2/2004 | Oldenburg et al. | 427/214 |
| 6,713,177 | B2 * | 3/2004 | George et al. | 428/402 |
| 6,746,510 | B2 * | 6/2004 | Kurihara et al. | 75/345 |
| 6,773,823 | B2 * | 8/2004 | O'Connor et al. | 428/548 |
| 6,783,569 | B2 * | 8/2004 | Cheon et al. | 75/348 |
| 2003/0143598 | A1 * | 7/2003 | Garimella et al. | 435/6 |
| 2005/0208142 | A1 * | 9/2005 | Zheng et al. | 424/489 |

OTHER PUBLICATIONS

Zhou et al, "Controlled synthesis and quantum-size effect in gold-coated nanoparticles", Physical Review B, vol. 50, No. 16, Oct. 1994, 12053-057.*

Zhou et al, "Nanostructure of gold coated iron core-shell nanoparticles and the nanobands assembled under magnetic field", Eur. Phys. J. D 16, 289-92 (2001).*

* cited by examiner

Primary Examiner—H. Thi Le
(74) Attorney, Agent, or Firm—Bruce H. Cottrell

(57) ABSTRACT

A process of preparing gold-coated magnetic nanoparticles is disclosed and includes forming a suspension of magnetic nanoparticles within a suitable liquid, adding an amount of a reducible gold compound and a reducing agent to the suspension, and, maintaining the suspension for time sufficient to form gold-coated magnetic nanoparticles.

13 Claims, No Drawings

GOLD-COATED NANOPARTICLES FOR USE IN BIOTECHNOLOGY APPLICATIONS

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to gold-coated nanoparticles and particularly gold-coated magnetic nanoparticles for use in biotechnology applications.

BACKGROUND OF THE INVENTION

In recent years, there has been an interest in using nanoparticles and magnetic nanoparticles for medicinal and biomolecular applications. U.S. Pat. No. 6,470,220 by Kraus, Jr. et al. described diagnosis and treatment of cancers using in vivo magnetic domains. This treatment approach employs a magnetic particle having a cancer-binding agent attached thereon. The cancer-binding agent should have binding specificity for the desired cancer cells. Such magnetic particles can be used as imaging agents in conjunction with magnetic resonance imaging (MRI), as a directing agent for therapeutics guided by external magnetic fields and for magnetotherapy techniques.

One prime candidate for the magnetic material is samarium cobalt. However, samarium cobalt has not previously been used as an agent within the body and has not previously been tested for biocompatibility. Thus, necessary governmental approvals would be required prior to the use of samarium cobalt.

Since samarium cobalt has such desirable magnetic properties for selected therapeutics and magnetotherapy techniques, a biocompatibly acceptable composition including a magnetic material such as samarium cobalt has been sought. After extensive and careful investigation, a composition has now been developed, in particular, a gold-coated magnetic particle composition.

It is an object of the present invention to provide a process of preparing a gold-coated nanoparticle composition, in particular a gold-coated magnetic nanoparticle composition for use in biotechnology applications.

It is another object of the present invention to provide a gold-coated nanoparticle composition, in particular a gold-coated magnetic nanoparticle composition for use in biotechnology applications.

SUMMARY OF THE INVENTION

To achieve the foregoing and other objects, and in accordance with the purposes of the present invention, as embodied and broadly described herein, the present invention provides a process of preparing gold-coated magnetic nanoparticles by forming a suspension of magnetic nanoparticles within a suitable liquid, adding an amount of a reducible gold compound and a reducing agent to the suspension, maintaining the suspension for time sufficient to form gold-coated magnetic nanoparticles. In another embodiment, the process further includes reacting the gold-coated magnetic nanoparticles with a mercapto-terminated bifunctional compound to form composite nanoparticles of a thiol-bound functional group-containing spacer group thereon the gold-coated magnetic nanoparticles. In still another embodiment, the process further includes reacting the functional group upon the composite nanoparticles with a linker group having one terminally protected functionality.

The present invention further provides a gold-coated magnetic nanoparticle composite including a magnetic nanoparticle central core, and, a coating of gold completely encapsulating said magnetic nanoparticle central core. In another embodiment, the composite further includes thiol-bound functional group-containing spacer groups thereon the gold-coated magnetic nanoparticles. In still another embodiment, the composite further includes linker groups bound at one end with said thiol-bound functional group-containing spacer groups thereon the gold-coated magnetic nanoparticles, the linker groups also having one terminally protected functionality.

DETAILED DESCRIPTION

The present invention is concerned with preparation of coated magnetic nanoparticles and a gold-coated magnetic nanoparticle composite. Such gold-coated magnetic nanoparticle composites have significant potential use in biotechnology applications. A gold coating would prevent direct bio-contact to the magnetic material thus improving biocompatibility. Also, a gold surface allows good coupling through chemical attachment of desired cancer binding agents.

By "nanoparticles" is meant, particles having dimensions of from about 10 nanometers (nm) to 250 nm, more preferably from about 10 nm to about 100 nm.

By "linker group" is meant to include a bifunctional molecule capable of covalently linking two other molecules to one another, e.g., bifunctional organic compounds such as $H_2N(CH_2)_nCOOH$ or $H_2N(CH_2)_nNH_2$ where n is an integer from 1 to 12, and the like, a terminally protected bifunctional organic compound such as $FmocHN(CH_2)_3NH_2$ and the like, glycols such as polyalkylene glycols, e.g., polyethylene glycol (PEG) or polypropylene glycol (PPG), and cysteamines and homologues thereof.

By "mercapto-terminated bifunctional compound" is meant to include compounds having a mercapto or thio group, typically at one end of a molecule, and another functional group such as a carboxylic acid, an amine, a sulfhydryl, a phosphate, a phosphonate hydroxyl, an alkenyl or an alkyne group, typically at another end of the molecule. Among suitable mercapto-terminated bifunctional compounds is 3-mercaptopropionic acid.

By "recognition group" is meant to include biological recognition elements including peptides (e.g., antibodies, antibody fragments and receptors), oligonucleotides, nucleotides, nucleic acids, polypeptides, proteins, and oligosaccharides that specifically recognize and bind a target molecule. In some instances, such recognition groups may be referred to as "biologically active molecules" such molecules from the group of a hapten, a biologically active ligand, a drug, a peptide, an oligonucleotide, a nucleotide, a nucleic acid, a polypeptide, a protein, an antibody, an antibody fragment and the like.

Among magnetic materials for use in the present invention are included magnetic materials from among the elements cobalt, iron, nickel, samarium, neodymium, platinum, boron, compounds thereof and alloys thereof. Ferromagnetic materials and rare earth containing materials such as, e.g., iron-cobalt (Fe—Co), iron-platinum (Fe—Pt), iron-cobalt-nickel (Fe—Co—Ni), samarium-cobalt (Sm—Co), neodynium-iron-boride (Nd—Fe—B) are suitable examples.

Other magnetic materials, e.g., superparamagnetic materials such as iron oxides ($Fe_3O_4$) may be used as well.

In the process of the present invention, the starting materials include a reducible gold compound and a reducing agent. Among suitable reducible gold compounds are included sodium terachloroaurate, sodium tetrabromoaurate, tetrachloroauric acid, tetrabromoauric acid, potassium tetrachloroaurate, and potassium tetrabromoaurate. Among suitable reducing agents are included sodium citrate, sodium borohydride, white phosphorus, lithium aluminum hydride, and sodium cyanoborohydride. Following coating of the magnetic material with gold, the composite can be reacted with mercapto-terminated bifunctional compounds to yield organic moieties upon the surface which can be modified using steps well known to those skilled in the art to provide suitable linkages to recognition groups and the like.

In a preferred embodiment of the present invention, samarium cobalt nanoparticles are coated with gold by admixture with a gold compound such as sodium tetrachloroaurate in combination with a suitable reducing agent.

The present invention is more particularly described in the following examples, which are intended as illustrative only, since numerous modifications and variations will be apparent to those skilled in the art.

EXAMPLE 1

Samarium cobalt ($SmCO_5$) nanoparticles (0.100 g; 0.225 mmol) were suspended in 25 mL of water with use of a sonic dismembrator (Fisher Model 60, 80–90 watts) at 0° C. Excess sodium terachloroaurate ($NaAuCl_4$) (0.820 g, 2.25 mmol) was added to the suspension and reduced to the metal using a freshly prepared solution of sodium borohydride (0.130 g, 3.44 mmol) in 50 mL of water. The resultant gold-coated $SmCO_5$ particles were separated from the co-produced gold nanoparticles by a permanent magnet and the gold-coated $SmCO_5$ particles were washed with three 25-mL portions of water. The gold-coated $SmCO_5$ particles were dried overnight under a high vacuum. Visual examination of the gold-coated magnetic nanoparticles showed that the magnetic nanoparticles were completely coated with a layer of gold.

EXAMPLE 2

A 15 mL centrifuge tube was charged with gold-coated $SmCO_5$ particles (0.1023 g) from example 1 followed by N,N-dimethylformamide (DMF) (5 mL) and 3-mercaptopropionic acid (0.7 mL, 8.0 mmol). The mixture was placed on a rotator overnight and then spun down in a centrifuge. The liquid was decanted off and the solid was washed with three 10-mL portions of DMF. The resultant coated-material included a free carboxylic acid group.

EXAMPLE 3

A 15 mL centrifuge tube with a cap was charged with the gold-coated $SmCO_5$ particles having free carboxylic acid groups thereon from example 2, 1-hydroxybenzotriazole (HOBt)/2-1H-benzotriazole-1-yl)-1,1,3,3-tetramethyluronium hexafluorophosphate (HBTU) (0.5 M in DMF, 3 mL) and diisopropylethylamine (2.0 M in N-methylpyrrolidone, 1.5 mL). The mixture was placed on a rotator for 30 minutes and then spun down in a centrifuge. The liquid was decanted off and the solid was washed with three 10-mL portions of DMF. N,N-dimethylformamide (5 ml) was added to the solid followed by addition of Fmoc-ethylenediamine hydrochloride (2.27 g, 8.04 mmol) diisopropylethylamine (2.0 M in N-methylpyrrolidone, 5 mL). The mixture was placed on a rotator overnight and then spun down in a centrifuge. The liquid was decanted off and the solid was washed with three 5-mL portions of DMF. The particles were dried overnight under a high vacuum.

EXAMPLE 4

The Fmoc label was cleaved using piperidine and monitored by UV to give the loading factor, i.e., the amount of accessible Fmoc groups per gram of material. The loading factor using this procedure was determined to be 0.06 mmol Fmoc per gram of labeled $SmCO_5$ particles. As a comparison, loading factors for commercial solid phase peptide synthesis support material are in the range of 0.2 to 5 mmol Fmoc per gram of support material. With $SmCO_5$ particles having more than a five-fold higher density than commercially available polystyrene resin core material, the loading of the gold-coated magnetic particles was within an expected range.

Although the present invention has been described with reference to specific details, it is not intended that such details should be regarded as limitations upon the scope of the invention, except as and to the extent that they are included in the accompanying claims.

What is claimed is:

1. A process of preparing gold-coated magnetic nanoparticles comprising:
   dispersing magnetic nanoparticles wherein said magnetic nanoparticles are of a magnetic material selected from the group consisting of the elements samarium, neodymium, compounds thereof and alloys thereof within a suitable liquid to form a suspension;
   adding an amount of a reducible gold compound and a reducing agent to the suspension; and,
   maintaining the suspension for time sufficient to form gold-coated magnetic nanoparticles wherein said gold coating is directly on said magnetic nanoparticles.

2. The process of claim 1 wherein said reducible gold compound is selected from the group consisting of sodium tetrachloroaurate, sodium tetrabromoaurate, tetrachloroauric acid, tetrabromoauric acid, potassium tetrachloroaurate, and potassium tetrabromoaurate.

3. The process of claim 1 wherein said reducing agent is selected from the group consisting of sodium citrate, sodium borohydride, white phosphorus, lithium aluminum hydride, and sodium cyanoborohydride.

4. The process of claim 1 further including reacting said gold-coated magnetic nanoparticles with a mercapto-terminated bifunctional compound to form composite nanoparticles of a thiol-bound functional group-containing spacer group thereon said gold-coated magnetic nanoparticles.

5. The process of claim 4 further including reacting said functional group upon said composite nanoparticles with a linker group having one terminally protected functionality.

6. The process of claim 5 wherein said linker group having one terminally protected functionality is selected from the group consisting of Fmoc-ethylenediamine, ethylene glycols, propylene glycols, cysteamines and homologues thereof.

7. The process of claim 5 wherein said linker group having one terminally protected functionality is Fmoc-ethylenediamine.

8. The process of claim 4 wherein said mercapto-terminated bifunctional compound includes as a functionality selected from the group consisting of carboxylic acid, amine, sulfhydryl, phosphate, phosphonate hydroxyl, alkenyl, and alkyne.

9. The process of claim 4 further including de-protecting the one terminally protected functionality and reacting said functionality with a recognition group, a bioconjugative reactive moiety or a biologically active moiety.

10. A process of preparing gold-coated magnetic nanoparticles comprising:
dispersing magnetic nanoparticles of samarium cobalt within a suitable liguid to form a suspension;
adding an amount of a reducible gold compound and a reducing agent to the suspension; and,
maintaining the suspension for time sufficient to form gold-coated magnetic nanoparticles wherein said gold coating is directly on said magnetic nanoparticles.

11. The process of claim 10 wherein said reducible gold compound is selected from the group consisting of sodium tetrachloroaurate, sodium tetrabromoaurate, tetrachloroauric acid, tetrabromoauric acid, potassium tetrachloroau rate, and potassium tetrabromoau rate.

12. The process of claim 10 wherein said reducing agent is selected from the group consisting of sodium citrate, sodium borohydride, white phosphorus, lithium aluminum hydride, and sodium cyanoborohydride.

13. The process of claim 10 further including reacting said gold-coated magnetic nanoparticles with a mercapto-terminated bifunctional compound to form composite nanoparticles of a thiol-bound functional group-containing spacer group thereon said gold-coated magnetic nanoparticles.

* * * * *